(12) United States Patent
John et al.

(10) Patent No.: US 8,700,142 B2
(45) Date of Patent: Apr. 15, 2014

(54) BRAIN FUNCTION SCAN SYSTEM

(75) Inventors: Erwin Roy John, Mamaroneck, NY (US); Michael Sasha John, North York (CA)

(73) Assignee: New York University, New York, NV (US)

(*) Notice: Subject to any disclaimer, the term of this patent is extended or adjusted under 35 U.S.C. 154(b) by 512 days.

(21) Appl. No.: 12/275,395

(22) Filed: Nov. 21, 2008

(65) Prior Publication Data

US 2009/0076407 A1  Mar. 19, 2009
US 2009/0227889 A2  Sep. 10, 2009

Related U.S. Application Data

(60) Continuation of application No. 10/045,799, filed on Jan. 10, 2002, now Pat. No. 7,471,978, which is a division of application No. 09/447,369, filed on Nov. 23, 1999, now Pat. No. 6,385,486, which is a division of application No. 08/908,456, filed on Aug. 7, 1997, now Pat. No. 6,052,619.

(51) Int. Cl.
*A61B 5/04* (2006.01)

(52) U.S. Cl.
USPC .......................................... 600/545; 600/544

(58) Field of Classification Search
USPC .................................................. 600/544–545
See application file for complete search history.

(56) References Cited

U.S. PATENT DOCUMENTS

| | | | | |
|---|---|---|---|---|
| 3,001,065 A | * | 9/1961 | Peterson | 178/116 |
| 4,094,307 A | * | 6/1978 | Young, Jr. | 600/544 |
| 4,201,224 A | * | 5/1980 | John | 600/544 |
| 4,279,258 A | * | 7/1981 | John | 600/544 |
| 4,412,547 A | * | 11/1983 | Callahan et al. | 600/544 |
| 5,522,386 A | * | 6/1996 | Lerner | 600/547 |
| 6,001,065 A | * | 12/1999 | DeVito | 600/544 |

* cited by examiner

*Primary Examiner* — Michael D'Angelo
(74) *Attorney, Agent, or Firm* — Fay Kaplun & Marcin, LLP

(57) ABSTRACT

A portable EEG (electroencephalograph) instrument, especially for use in emergencies and brain assessments in physicians' offices, detects and amplifies brain waves and converts then into digital data for analysis by comparison with data from normal groups. In one embodiment, the EEG electrodes are in a headband which broadcasts the data, by radio or cellular phone, to a local receiver for re-transmission and/or analysis. In another embodiment, the subject is stimulated in two modes, i.e., aural and sensory, at two different frequencies to provide the subject's EPs (Evoked Potentials), assessing transmission through the brainstem and thalamus.

11 Claims, 5 Drawing Sheets

BRAIN FUNCTION SCAN SYSTEM

PRIORITY CLAIM

The present application is a Continuation application of U.S. patent application Ser. No. 10/045,799 filed on Jan. 10, 2002 entitled "Brain Function Scan System" which is a Divisional of U.S. patent application Ser. No. 09/447,369 filed on Nov. 23, 1999 now U.S. Pat. No. 6,385,486 issued on May 7, 2002; which is a Divisional of U.S. patent application Ser. No. 08/908,456 filed on Aug. 7, 1997 now U.S. Pat. No. 6,052,619 issued on Apr. 18, 2000, the entire disclosures of these applications are expressly incorporated herein by reference.

BACKGROUND OF THE INVENTION

1. Field of the Invention

The present invention, called a "brain stethoscope", relates to a medical apparatus and more particularly to a portable EEG (electroencephalograph) device to detect, amplify and analyze brain waves generated by a human and to transmit the results to a remote receiver.

2. Related Art

It has become evident that human brain electrical activity is precisely regulated by a complex brain homeostatic system. Normative values are precisely predictable and have been found to be independent of ethnic factors. Characteristic patterns of deviation from such normative values have been reported for a wide variety of developmental, neurological and psychiatric disorders.

At the present time it is difficult for emergency personnel to determine if a subject has suffered injury to the brain or the spinal cord, cerebrovascular obstruction (stroke) or hemorrhage (bleeding). If these conditions could immediately be identified, patients' lives may be saved through rapid and appropriate treatment, usually determined after a subsequent neurological exam. The causes of abnormal behavior such as violent outbursts are often similarly ambiguous.

It is usual, during a routine medical examination, to evaluate the heart using an EKG (electrocardiogram) device. Usually, there is no attempt to determine if the patient has any brain dysfunction or conditions that may be discoverable using an EEG (electroencephalograph), as generally such devices produce an analog wavy set of waveshape tracings which must be interpreted subjectively by skilled electroencephalographers. Consequently, although the patient may be suffering from brain damage or dysfunction, such as a tumor, it is often not detected in the course of the medical examination. The absence of information about central nervous system (CNS) dysfunction often results in suboptimal treatment.

As an example, a patient arrives at a hospital emergency room (ER) with certain physical symptoms of ischemic stroke, or "brain attack", resulting from blocked blood flow to the brain. Unless the patient is treated promptly, brain cells in the ischemic region would continue to be deprived of oxygen, possibly destroying parts of his cognitive abilities, memory and motor skills and possibly resulting in death. Such adverse effects of ischemic stroke may be halted by immediate and appropriate treatment, for example, injection of tissue plasminogen actuator (tPA), which dissolves clots. However, tPA treatment of a possible stroke victim may be hazardous to initiate, as his physical symptoms may be caused by an intracerebral hemorrhage which can be worsened by dissolving clots. Quantitative analysis of the EEG (QEEG) may provide a rapid and objective diagnosis between these alternatives.

As another example, a person may be in a coma when emergency ambulance personnel (EMS) arrive. He should not be moved if he has suffered spinal injury. But the ambulance personnel cannot determine if he has suffered spinal injury by simply looking at the comatose patient. Somatosensory evoked potentials (SEPs) provide assessment of the functional integrity of the spinal cord.

Another example of the need for an objective and immediate brain assessment is in situations where there are a number of injured persons who may require medical attention, some of whom may be in a coma. For example, on the battlefield or in the event of a train wreck, it may be necessary to separate comatose patients who are breathing and viable and require immediate treatment, from those who are still breathing but are brain dead. And again, in that situation, it is important to tell if a patient who is comatose but alive has a spinal injury, so that he should not be moved. QEEG, SEPs and brainstem auditory evoked response (BAERs) may provide a rational basis for triage in such situations.

A series of publications and patents in the name of Dr. E. Roy John relate to the field of EEG "neurometrics", which is quantitative electrophysiological measurements (QEEG) evaluated relative to normative data. Generally, a subject's analog brain waves, at the microvolt level, are amplified, artifacts removed and the amplified brain waves converted to digital data. That data is then analyzed in a computer system to extract numerical descriptors which are compared to a set of norms (reference values), either the subject's own prior data (initial state) or a group of normal subjects of the same age (population norm). Such analyses can quantify the level, if any, of deviation of the activity of any brain region from the reference values.

A computer system based instrument using those principles is the "Spectrum 32" (Cadwell Instruments, Washington). That instrument is large, non-portable and relatively expensive (tens of thousands of dollars). It is generally used by experienced neurologists in a neurology clinic or hospital neurology department. It is not suitable for use in an ambulance, emergency room or a doctor's office for regular medical examinations. Some of the aforementioned patents which relate to neurometrics are U.S. Pat. Nos. 4,279,258; 4,846,190; 4,913,160; 5,083,571 and 5,287,859, incorporated by reference.

There are a number of patents directed to determine whether a person is alive. For example, Allain U.S. Pat. No. 5,029,590 discloses the use of a pocket-size monitor for life detection. The Allain patent deals primarily with detecting heartbeat via EKG and mentions detecting brain waves using EEG.

In John U.S. Pat. No. 3,706,308 entitled "Life Detecting Medical Instrument" a portable device has EKG and EEG monitors, a stimulator for evoked brain responses (Evoked Potential—EP), an average response computer and a visual display. It determines if a patient is legally dead by comparison of the patient's brain waves with predetermined standards of brain death and does not use comparisons with normal values.

There is an existing need for a portable self-evaluating EEG and EP device which can be monitored by a hand-held control distant from the patient. For example, where an injured person's heartbeat cannot be detected or he is in a coma, he may be taken to a hospital, which has an EEG device and neurologist to detect and evaluate brain waves and to determine whether he is alive and whether his brain is injured. However, in some emergencies, medical personnel need to quickly determine if a patient has had a stroke or if the patient is alive but in a coma, or dead, or if a person has suffered spinal injury. A particular difficulty arises when some patients have spinal injury and are unconscious. In those cases, it would be difficult for medical personnel to ascertain who can safely be moved or should not be moved because of spinal injury. Persons with such conditions may die due to the lack of medical information, for example, a non-spinal injury patient may be in a coma and is not properly and timely transported to a hospital, or may become paralyzed if moved with unrecognized spinal injury.

In general, there are numerous instances in which the ability to make a "brain scan" by a portable EEG/EP device ("Brain Stethoscope") could be valuable in assessing the probability of abnormal brain function rapidly and automatically.

SUMMARY OF THE INVENTION

In accordance with the present invention, there is provided a portable EEG device which can accurately, reliably, continuously and quickly determine if the patient is in a coma, is suffering from concussion or is brain dead; if he is having an ischemic stroke or an intracerebral hemorrhage; if he has a serious spinal injury; and, if his behavior is of concern, whether he has abnormal brain function.

In one embodiment of the present invention, called "Version 1", intended especially for use by emergency personnel and emergency vehicles, in hospital emergency rooms and family physician offices, an EEG device has a limited number of EEG electrodes and may have an EKG electrode, preferably lead 2, and may receive input from a blood pressure device, such as a finger plethysomometer or blood oxygen or saturation meter. Depending upon the particular application, arrays of 1-16 head electrodes may be used, as compared to the International 10/20 system of 19-21 head electrodes generally used in a conventional BEG instrument. The device is small, preferably hand-held, and relatively simple, easy to use and inexpensive. It includes a software programmed microprocessor having a CPU (Central Processor Unit) which performs the following functions: (i) it steps (polls) through the EEG electrodes if more than one electrode is used, so that each symmetrical pair of electrodes (e.g., P3 & P4) is connected simultaneously (electrode pairs are polled in sequence and the instrument is a two-channel or four-channel device) and evaluates the spontaneous EEG; (ii) it provides a timed sequence of concurrent stimulations in one or two sensory modalities (modes) to the patient, such as an audio tone or click at one repetition rate ($F_1$) and electrical shocks to peripheral nerves at a second repetition rate ($F_2$); (iii) based on the responses to these multimodal stimulations, it tests the functional state of the spinal cord (SSEP—Somatosensory Evoked Response) and brain stem (Brain Stem Auditory Evoked Response—BAER); and (iv) it assesses the cardiac rhythm.

Preferably, stimulations are used in two different modes, i.e., auditory clicks and electric pulses to the skin. The stimuli, although concurrent, are at different prime number frequencies to permit separation of different EPs and avoid interference. Such concurrent stimulations for EP permit a more rapid, and less costly, examination and provide the patient's responses more quickly, which is important in emergency situations. Power spectra of spontaneous EEG, waveshapes of Averaged Evoked Potentials, and extracted measures, such as frequency specific power ratios, can be transmitted to a remote receiver. The latencies of successive EP peaks of the patient may be compared to those of a normal group by use of a normative template.

Preferably, to test for ischemic stroke or intracerebral or subarachnoid hemorrhage, the instrument includes a blood oxygen saturation monitor, using an infra-red or laser source, to alert the user if the patient's blood in the brain or some brain region is deoxygenated.

Another embodiment, called "Version 2", is particularly for use in field conditions in which an immediate indication of brain damage is desired from a number of persons, some of whom may be unconscious. An adhesive patch, or headband, is placed on each subject. It contains one, or more, EEG electrodes, an amplifier, and a local radio transmitter. A stimulus device may optionally be placed on each subject, such as an audio generator in the form of an ear plug, which produces a series of "click" sounds. The subject's brain waves are detected, amplified and modulate the transmitter's carrier wave. A hand-held radio receiver receives the radio waves, demodulates them and converts them into audio tones. The receiver may have an array of LED (Light Emitting Diodes) which blink depending on the power and frequency composition of the brain wave signal. Power ratios in the frequencies of audio or somatosensory stimuli are similarly encoded. With the proper training, brain wave modulated tone signals can be immediately recognized as being generated by an intact brain or an injured brain. A physician or medical aide who is properly trained to use the Brain Stethoscope may determine, either by reading the LCD screen, listening to the audio tones, or by looking at the blinking LEDs, whether the patient's brain function is abnormal and may evaluate the functional state of various levels of the patient's nervous system.

Another embodiment, called "Version 3", uses a headband (or patch) and a hand-held receiver. The headband has 2-16 BEG electrodes, an amplifier for each electrode, an A/D (Analog/Digital) converter and a local radio transmitter. The transmitter broadcasts an FM or AM carrier which is modulated by the digital data, from the A/D converter, representing the subject's brain waves. The hand-held receiver performs the functions of analyzing the brain waves and stimulating the subject. It includes a display and a microprocessor board. The type of brain wave analysis and stimulation may be the same in Version 1.

In another embodiment, called "Version 4", the EEG device has a single electrode on a headband or an adhesive patch which is placed on a person's head to detect brain waves which are amplified and transmitted by a micro-transmitter to a microprocessor within a hand-held receiver. The microprocessor analyzes the power spectrum of the brain waves by comparison to predetermined norms, or by various ratios of power in different frequency bands. Version 4 preferably also includes a second patch having an EKG electrode and amplifier. Either or both patches may carry an A/D converter and microtransmitter, the second patch being placed on the skin above the left collarbone.

The hand-held receiver may have LEDs, or a display panel, which displays the results of the analysis, or an audio output.

In "Version 5" a single electrode is placed preferably midway between the ears. A patch containing the electrode also has an amplifier, an A/D converter, microprocessor and a display. The microprocessor analyzes the digital data and indicates if the subject's brain waves are normal or abnormal. This Version 5 may be especially applicable in a battlefield situation.

The invention may be especially useful in cases of an emergency, for example, a wartime or peacetime explosion/disaster situation where a large number of people are injured or dead. The portable EEG device analyzes the power spectrum of brain waves to assist evaluating the degree of injury. By utilizing the portable EEG device, medical personnel may, for example, quickly divide patients into four categories:

dead, seriously injured who must be moved to a hospital immediately, injured who can be moved to a hospital later, and injured, who should not be moved without special precautions.

One advantage of the portable EEG device is that it allows personnel at the scene of an emergency to determine almost instantly whether a person is alive but suffering from concussion; is having an ischemic stroke or is suffering intracerebral bleeding; if the person is dead or in coma; whether the patient has brainstem or spinal injury; or if the patient does not have a heartbeat. The device may be utilized by medical personnel in the field, ambulance medical personnel, firemen and policemen as well as other emergency room personnel, and may be relatively simple to use and low in cost. The instrument, when used in emergency vehicles, such as firetrucks and ambulances, preferably has a built-in cellular telephone which automatically dials-up or otherwise transmits its data to a neurometric computer, for example, at a hospital. Thus, while providing immediate automatic evaluation of patient's brain state at the emergency site, it can transmit a series of brain measurements which are continuously updated to construct a "state trajectory" for remote evaluation by qualified specialists.

DETAILED DESCRIPTION

Version 1

Figure 1:
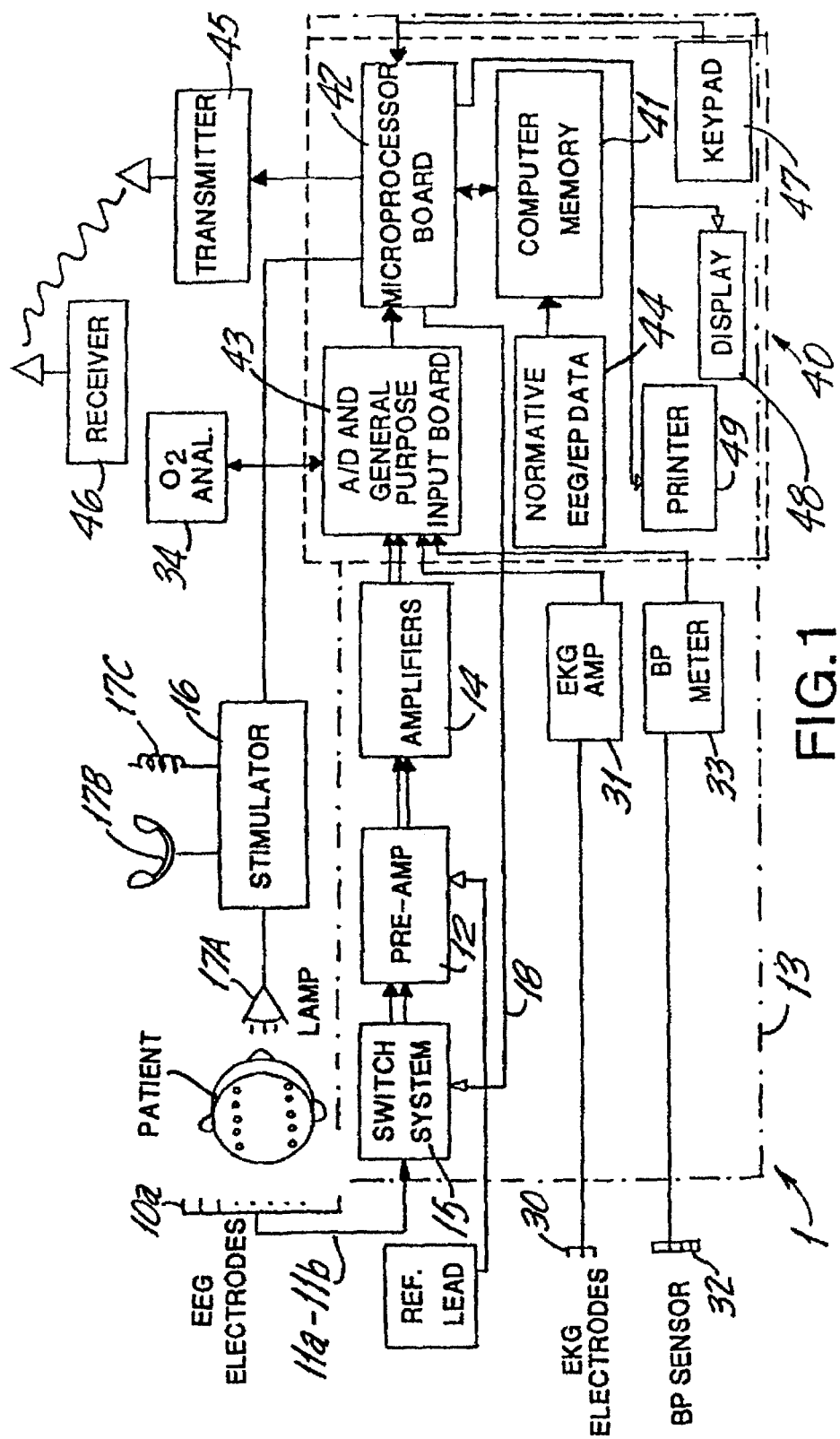
FIG. 1 is a block electronic schematic drawing of the system of the first embodiment.

In the first embodiment, shown in FIG. 1, the instrument 1 is a small and inexpensive device which is portable and may be hand-held. It uses a computer system based on a conventional microprocessor, such as an Intel Pentium I™ and has a limited internal memory, for example, 100 MB.

The instrument 1 has 1-24 EEG amplifiers, each of which may be connected to a removable EEG electrode shown as electrodes 10a-10p. A suitable electrode uses an adhesive cover, which is removed before applying it to the scalp. The electrode may have multiple small barbs, a needle electrode or a conductive disk, which is removably attached to and may penetrate the patient's skin; the electrode may also use conductive gel, providing rapid attachment and acceptably low impedance, and may be sterile and disposable. In this, and other embodiments, a self-adhering electrode may be used, for example, the "ZIP-PREP"™ electrode having stainless steel micro-barbs in an adhesive gel patch, the patch being applied with finger pressure.

As shown in FIG. 1, each of the electrodes 10a-10p is connected to a lead 11a-11p which is connected, within the instrument casing 13, to a low-noise programmable multiplexer or electronic switch 15. The programmable switch 15 may have multiple input lines and one or more output lines and is controlled by the microprocessor (CPU) board 42.

The output lines of switch 15 are connected, to a one-, two- or four-channel low noise preamplifier 12 and to a one-, two- or four-channel amplifier 14. The amplifier 14 is connected to an analog-to-digital converter (A/D) and multiplexer within General Purpose Input Board 43 (GPIB).

Preferably the electrodes are in a stretch hat, elastic flexible band or helmet. The number N of electrodes is generally greater than the number of amplification channels. However, with micro-miniaturization and reduction in cost of amplification channels, each electrode may be connected to its own amplification channel. As many as, but not limited to, 24 electrodes, or as few as one, may be used and as few as one amplification channel, or as many as N, may be used.

The computer system 40 includes a GPIB (General Purpose Input Board) 15 and a microprocessor board 42. The CPIB includes an analog-digital converter (A/D) and multiplexer 43. The computer memory 41 contains a normative or reference EEG and EP database 44. Results stored in the computer memory or other storage means can be transmitted as a digital signal by telephonic or radio transmitter 45 to a remote receiver 46, and may be encoded as audible or visual signals presented by the display 48.

A printer 49 may be used to print out a report on the patient. Preferably the printer is a color printer which is used to generate a topographic "heat scale" color-coded map of the patient's head showing, by its colors, the patient's statistical "normal" and "abnormal" regions.

The analog-to-digital multiplexer (A/D multiplexer) provides a digital output from the analog amplifiers. The A/D multiplexer samples the EEG waves (outputs of amplifiers) at a rate preferably in the range of 200 to 300 times per second (or 5 KHz for BAER+SSEP).

The data from the multiplexer is transmitted to a microprocessor board 42. The microprocessor has been programmed by an external software program means, such as a floppy disk recorder, or other input system, such as read-only memory (ROM). The programmed microprocessor ("firmware") is programmed to perform the data acquisition and the data analysis described below. The keypad 47 is used to enter the patient's age, name and other information.

The program and its controlled microprocessor condition the input signals and insure that they are valid biological signals, including automatic artifact rejection, and periodic automatic calibration testing and impedance measurements.

The patient is stimulated by the stimulator 16 under control of the microprocessor board 42 of computer system 40. The stimulator 16 may be a lamp 17A which is flashed. In addition, or alternatively, other stimulus devices, such as headphones 17B for auditory stimulation and vibratory device 17C or low level voltage electrical skin stimulation devices may be used.

The computer system 40 automatically provides a timed set of stimuli of various modalities for the stimulator. Stimuli may be delivered separately in each modality or concurrently but at frequencies $F_i$ which are prime numbers which share no common harmonic (see FIG. 4). The patient's brain waves will respond to each stimulus with a component at frequency $F_i$ in the EEG power spectrum, providing an "Evoked Potential" (EP). Those brain waves may be averaged, time locked to stimuli onsets to improve the signal/noise ratio, providing an "Average Evoked Response" (AER) Filtering and splitting algorithms may reduce low frequency noise and remove artifact contaminated samples prior to averaging.

The AER is the sum of N samples time locked to the onset of stimuli divided by the number of samples, to provide an updated average. N will vary depending upon the usual signal to noise ratio in each sensory modality. The AER's are held in computer memory 41.

Alternatively, narrow band FFT may be used to compare the power in the EEG at frequencies $F_i$ when the stimulator is on vs. off, using an F-ratio.

The device described herein is capable of evaluating both the spontaneous electrical activity of the resting brain (EEG) and the processing of unimodal or multimodal sensory information after stimulation (EPs).

The switch system 15 is controlled over line 18 by microprocessor board 42. It switches the electrodes 10a-10p to the preamplifiers 12. For example, if 3 preamplifiers are used, one is used for common reference fiducial (vertex lead), such as position $C_z$ and the other two channels are automatically switched, by the microprocessor 42, between selected electrodes. In this way, one amplifier compresses several channels.

Each of the preamplifiers has an input isolation circuit to protect against current leakage, such as a photo-diode light-emitting diode (LED) isolation coupler. The preamplifiers are protected from electrical interference by a radio-frequency filter and a 60-cycle notch filter. Preferably each preamplifier has a computer-controlled switchable frequency range of 0.5 to 100 Hz, gain of 10,000, or of 100 Hz-5 KHz with gain of 100,000, common mode rejection of 106 dB, and noise of less than 1 microvolt.

EEG recordings may be contaminated by voltages arising from body movements, eye motion or other causes. These artifacts, it is assumed, based on prior studies, generate voltages larger than the brain wave voltage. An updating voltage threshold is computed continuously for each EEG channel, separately, by calculating the root mean squared (rms) voltage, for example, for a sliding 20-second window and multiplying it by an appropriate constant (rms voltage is approximately 0.2 standard deviations of amplitude). Segments containing voltages larger than this updated threshold are rejected, unless this option is turned off or the criteria altered by attending personnel. Sampling is suspended after the threshold is exceeded, for example, for one second, to avoid increasing the threshold by incorporating the artifact. It is then resumed. Preferably, those intervals (recording periods on each EEG channel) are rejected in which the voltage (signal) exceeds a multiple of the rms voltage equal to 6 times (6×) the standard deviation of amplitude. Alternatively, an absolute maximum voltage threshold may be installed. This voltage threshold method provides segments of relatively artifact-free EEG data. The computer system, in effect, stitches these intervals together to form a continuous artifact-free EEG sample, which is recorded in the computer memory.

Because critical decisions may depend upon the accuracy of the Brain Stethoscope evaluation, ideally odd and even "split half" samples may be constructed by assigning intervals to alternately interloaded but independent samples. For example, the samples from each electrode lead are 2.5 seconds long, the first sample is even-numbered, the second sample is odd-numbered, etc. Then the odd-numbered samples and even-numbered samples are individually compared with the norms. If a true dysfunction exists the measures revealing it must be reliably replicable. An abnormality is defined with significance of P<0.05, for example, "Abnormal" is defined as deviant from normal at the 0.05 level. For example, a "split-half" consists of the first (odd) P1 and second (even) P2 samples. To be "abnormal" the same variable, at the same electrode, must be abnormal (at the 0.05 level) in both split-half samples. The probability that this could occur by chance is P1×P2 (0.05×0.05) or 0.0025. Results from the two split halves may be combined for display, with replicated significant results highlighted.

In addition, and optionally, the instrument may have sensors to determine the heartbeat rate, the blood pressure and the blood oxygen level of the subject. As shown in FIG. 1, one or more EKG electrodes 30 are connected to an EKG amplifier 31, with a bandwidth from 0.5 to 5000 Hz and a gain of 1000, which is connected to an input board 15. As explained below, the heartbeat QRS peaks and the R-R intervals are detected and displayed. A blood pressure (BP) sensor 32 is connected to BP meter (amplifier) 33, which is connected to input board 15. Preferably the BP sensor 32 is a finger tip blood pressure plethysmometer (plethysmograph). An oxygen analyzer 34 ($O_2$ ANAL), which is an optional device, is connected to input board 15. A suitable oxygen analyzer (blood oxygen saturation monitor) uses an infra-red or laser source to measure oxygen in the blood in body tissues or the brain. For example, the INVOS cerebral oximeter is available from Somanetics Corp., Troy, Mich.

The Brain Stethoscope of Version 1 can be used in three different modes. Mode 1 is concerned with evaluation of a patient who has possibly suffered traumatic brain/spinal cord injury. Mode 2 is concerned with evaluation of a patient at risk for ischemic stroke (infarct) as against intracerebral hemorrhage. Mode 3 is concerned with the evaluation of overall brain state in patients at risk for a variety of brain dysfunctions, ranging from substance abuse to attention deficit to depression to dementia to psychosis. The same basic hardware and artifact rejection, data acquisition and analysis software in the Brain Stethoscope is used in all three modes of application, but different lead configurations are required and different software programs are activated in the microprocessor, depending on which application is required.

Mode 1: In evaluation of traumatic brain/spinal cord injury, only three electrodes are required: one electrode on the vertex (Cz) one on the mastoid (left or right) and one on the forehead as ground. One channel of amplification will suffice, with a bandwidth of 0.5 Hz to 5 KHz, recording Cz versus the mastoid reference. The amplifier output is split into a low-pass EEG channel (0.5 Hz to 70 Hz) and a high pass (100 Hz to 1500 Hz) brainstem evoked response channel. The A/D sampling rate should be commensurate with these bandwidths. Auditory clicks, for example, at F1, (40/sec) and 90 dB should be delivered binaurally via stereophonic earphones for 30 seconds every minute. Electrical constant current shocks, for example, at F2, (27/sec), 0.5 mS, 20 mA, should be delivered to the fingertip of the right index finger or big toe by an electrode pair imbedded in a finger or toe cot, for the 30 seconds every minute when auditory clicks are not being delivered. Preferably a second channel is added for EKG (Lead 2), finger blood pressure plethysmomometer, or pulse oximeter, and switched between these inputs to provide information about heart rate, blood pressure and oxygen saturation which is useful to assess shock.

Analysis of Mode 1 Data: The EEG recordings obtained during the evaluation period should be analyzed using very narrow band FFT (Past Fourier Transform) in narrow, for example, 0.5 Hz increments (steps) from 0.5 Hz to 50 Hz. The power in the low delta (0.5-1.5 Hz), delta (1.5-3.5 Hz), theta (3.5-7.5 Hz), alpha (7.5-12.5 Hz), beta (12.5-20 Hz) and high beta (25-50 Hz) frequency bands should be computed and expressed as absolute ($\mu V^2$) and relative power (% of power from 1.5 to 20 Hz). EEG segments in which low delta power exceeds 2 times delta power or high beta power exceeds 2 times beta (absolute power) are rejected as contaminated by eye or muscle movements. The approximate age of the patient should be entered via the keypad 47 of the device. Using age-regression equations or normal mean values stored in a table in the normative database 44 (stored in ROM of the microprocessor), the Z score of each of the four bands should be computed, where Z=[N−P]/6 and N=normative mean value for a healthy population the same age as the patient, P=mean value computed from patient data and 6=standard deviation of the normal population values. For traumatic brain injury, positive Z-scores are expected for the delta and theta bands. These values are displayed on the screen of display 48 and transmitted to the receiving station 46 and tracked by a frequently updated (1/minute) trajectory. Increasing Z-scores for delta and/or theta suggest increasing intracranial pressure from edema or intracranial hemorrhage and may require neurosurgical intervention. For ischemia, positive Z-scores are expected in the theta band.

Using very narrow band (VNB) FFT, the power at F1 and F2 is computed every 10 seconds, averaged separately for the 30-second alternating periods of auditory click stimulation at frequency F1 and electric shock stimulation at frequency F2. Preferably the (VNB) FFT is computed at increments (steps) in the range 0.05-0.2 Hz and most preferably at 0.1 Hz (1/10 sec. sample). Taking advantage of the fact that EEG power at a given frequency equals the variance at that frequency, the ratios of power responsive to auditory stimulation F1 (on/off) and somatosensory stimulation F2 (off/on) are calculated. Alternatively, auditory stimuli at F1 and tactile stimuli at F2 are continuous, providing a steady state response. 10-second samples of EEG are collected, FFT computed at 0.1 Hz increments and an average of N samples of the FFT is computed. The power in the $F_1$ and $F_2$ windows (Fstim) and the average power in the windows, for example, 40 bins (B) above and below each of the stimulation frequencies, Fav, is used to compute the value of $$B = \frac{\text{Power } Fstim}{\text{Power } Fav}.$$

This latter method may be more rapid and sensitive. These ratios, treated as F-values, permit statistical assessment of the probability that the auditory stimuli are traversing the brainstem and the somatosensory stimuli are traversing the spinal cord and brainstem to reach the cerebral cortex. In addition, using trigger pulses at the F1 and F2 frequencies, the microprocessor computes the averaged brainstem auditory evoked responses (BAER) and somatosensory evoked responses (SSER). The averaged BAER and SSER waveshapes, together with the full power spectrum, encoded delta, theta, alpha and beta Z-scores and the F-values for the F1 and P2 power in the EEG, are all transmitted to a remote receiving station 46 for updating a display (compressed spectral and EP waveshape arrays and feature trajectories) and for evaluation relative to normative templates (comparison with normal groups).

Figure 7:
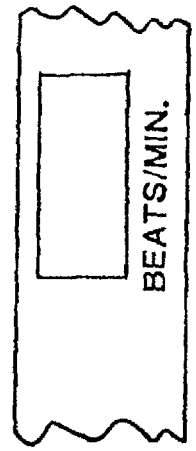
FIGS. 7, 8 and 9 are top plan views of alternative displays for the instruments of FIG. 1, 2, 3, 5 or 6.
Figure 8:
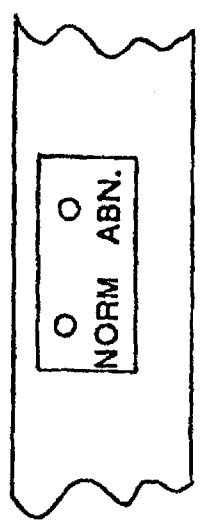

For analysis of EKG, QRS peak would be detected and R-R interval calculated for heart rate, displayed on an LCD, shown in FIG. 7, as BEATS/MIN.

Mode 2: The detection of ischemic stroke or intracerebral hemorrhage (bleed) is based upon the basic EEG signs of such cerebrovascular events, arising from the breakage or blockage of a blood vessel. Such events are usually on one side of the brain and give rise to asymmetry in slow brain waves. The electrodes are arranged in symmetrical (homologous) pairs, one electrode of each pair being on the left side of the head and the other electrode being on the right side of the head. In the absence of ischemic stroke, generally the slow waves from both electrodes are equal in amplitude and in phase, i.e., symmetric and synchronous. In this mode, pairs of homologous (L/R) electrodes are polled, preferably in sequence starting from the front (frontal, temporal, central, parietal, occipital). If any electrode pair shows consistently asymmetric slow waves, especially in the theta band, it is a sign of possible cerebral ischemia. Using increments of 2.5 second artifact-free EEG segments, a sliding window 20 seconds wide is constructed and the average Z-scores of delta, theta, alpha, beta absolute power and relative power and their asymmetries are calculated across the segments within this window. Split-half replication between samples constructed from alternate odd and even segments may be used to validate results by replication, as described for Mode 1. These sequential Z-scores and their Left/Right ratios (asymmetries) are used to construct a state trajectory for each region (electrode). If the slow wave asymmetry rapidly asymptotes to an approximately constant value, or if the absolute or relative power Z-score (especially for theta or delta) in a given region reaches a stable abnormal value (dz/dt>0), the cerebrovascular event is probably occlusion of a vessel (stroke); but if it continues to exacerbate or spread to adjacent regions (dz/dt 0), it is probably a hemorrhage (bleed) which may require rapid intervention. Once the probability of stroke rather than bleed is established, the patient should immediately be treated, for example, with tPA. Successful thrombolytic treatment may restore normal symmetry and Z-values.

Mode 3: In order to obtain a comprehensive QEEG evaluation of brain state, it is advisable to scan the EEG in 8 pairs of homologous electrode placements (FP1/FP2, F3/F4, C3/C4/, P3/P4, O1/O2, F7/F8, T3/T4, T5/T6). Each pair of electrodes provides a short period sample, for example, 1-10 seconds and preferably segments of about 2.5 seconds (artifact free). A fiducial electrode, preferably the electrode at position cz is recorded continuously to confirm stationarity during the full scan. Preferably, linked earlobes (A1+A2) are taken as the reference. The electrodes are scanned in pairs a number of times, for example, 8-48 times and preferably at least 24 times, and ideally 48 times, for a total of 120 seconds/pair. In a two-channel 16-electrode system (8 pairs) at 2.5 seconds per segment per pair, each scan takes 20 seconds. The scans may be performed by an electronic switch, as shown in FIG. 1. The ideal 48 scans take 960 seconds, or 16 minutes, and the minimum 8 scans required for high reproducibility would take 160 seconds. In a four-channel system, the corresponding scan times would be 480 seconds and 80 seconds. The trade-off between cost (number of channels) and scan time may involve 2, 4, 8 and 16 channel versions of the Brain Stethoscope for use in situations where rapidity of Mode 3 applications may be important. One additional EEG channel should be dedicated to continuous Cz recording.

For each of the 2.5 second segments during the total scan, the values of the EEG spectral parameters are computed for Cz, which is recorded in every scan, and the mean M and standard deviations 6computed across the set of segments in the scan. Any segment for which a parameter of Cz exceeds M+2.5 6 should be excluded from the scan. Replication between odd and even split half samples may be used to further establish validity of abnormal findings, as described for Mode 1. Taking advantage of the demonstrated stationarity of the resting EEG, the digital data averaged across the full scan is then compared with norms (population norms) to determine if the patient's brain function is normal or abnormal. A composite 16 channel scan is constructed from the multiple pairwise scans. The averaged spectral parameters for each lead and samples of raw data may be transmitted, by cellular phone or other transmission means, to a receiving PC terminal in a hospital neurology department or neurological center having a suitable computer for its analysis, such as the "Spectrum 32" (Cadwell Instruments) or any computer with neurometric capability. Interpolated statistical probability maps, color coded for significance using a "heat" scale, may be constructed at the remote receiver. Alternatively, the instrument 1 performs its own basic analysis on pairwise data and constructs the composite total scan and may also construct a topographic map, and preferably provides a simple result, i.e., "normal" or "abnormal", which may be followed by such transmission.

The criteria for "normal" and "abnormal" functions may be a "look-up" table. For example, if the power at any electrode is significantly ($Z \geq 2.0$) below the norm, for the age group of the patient, then the patient is considered "abnormal" and an indication (colored light, digital read-out, buzzer, etc.) will be generated. More specific diagnostic classifications may require transmission of selected clinical observations to a remote center for specialized evaluations.

Further evaluation by the instrument's computer memory may have a set of discriminant functions. Such functions may be empirically derived and installed in the instrument. In one embodiment, the discriminant functions are held as a set in memory as a band or base number for each diagnostic category, see U.S. Pat. No. 5,083,571 at columns 4 and 5. For example, in the diagnostic category of ischemic stroke, the groups may be: normal (no stroke), cerebrovascular compromise (stroke) and intracerebral hemorrhage (bleed).

Version 2

Figure 2:
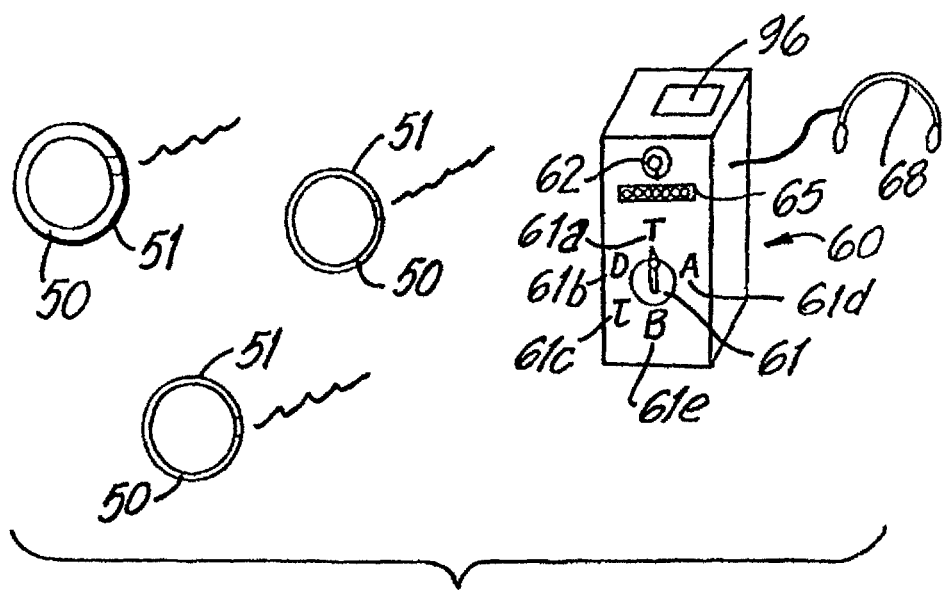
FIG. 2 is a view of the headband and hand-held instrument of the second embodiment of FIG. 2.
Figure 3:
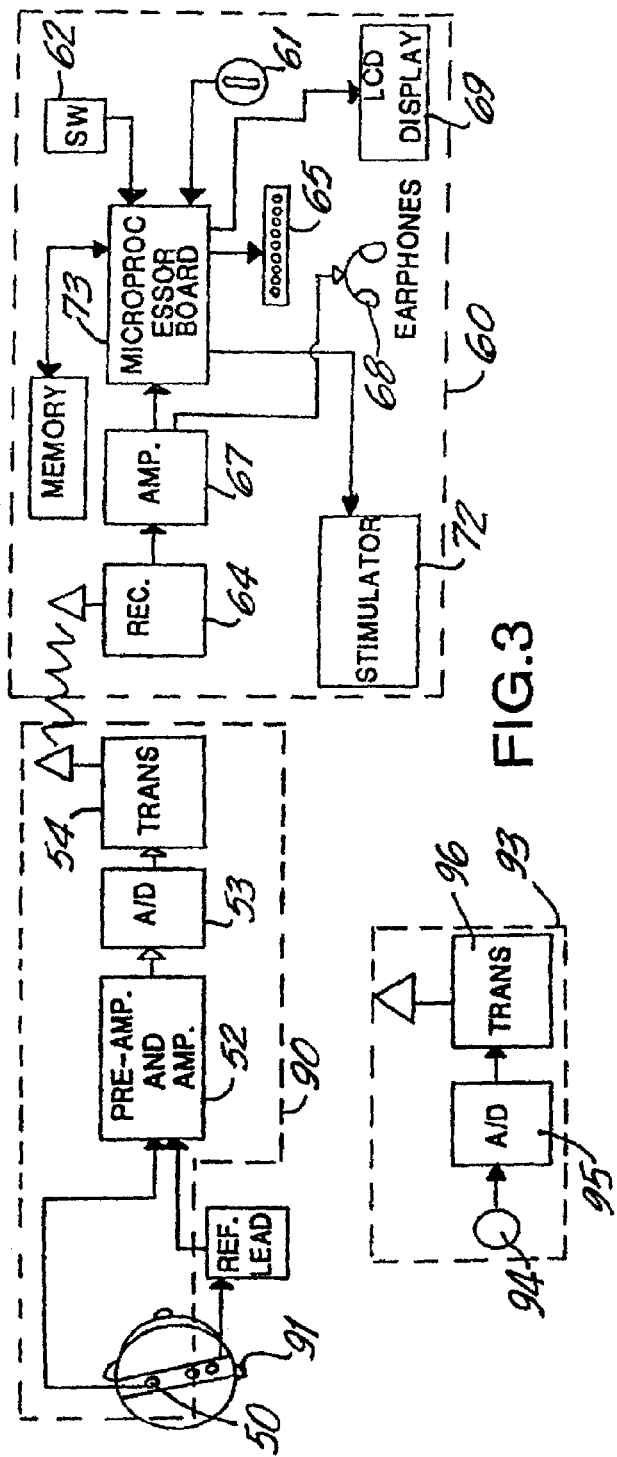
FIG. 3 is a block electronic schematic drawing of the system of the third embodiment.

The embodiment of FIGS. 2 and 3 is especially adapted for emergency personnel, such as firemen, military medical corpsmen, etc. It has only one self-adhering electrode 50, or a few such electrodes in a headband 51 or cap. The electrode 50 is connected to a tiny amplifier and radio-transmitter 54. The amplifier includes a pre-amplifier and high-gain amplifier 52 whose output after A/D conversion 53 modulates the AM transmission of the radio transmitter 54. The entire circuit unit (amplifier and transmitter) is preferably less than 0.25 inches thick and the size of a half-dollar.

The transmitter 54 may be small as it transmits only within a short range, for example, 50-300 feet. As shown in FIG. 3, a receiver unit is within a casing 60 which may be handheld and includes a radio receiver 64 tuned to the transmission frequency of the transmitter 54. The unit 60 also includes an amplifier 67 to amplify the demodulated signal and to drive a speaker or earphone (headset) 68. A switch 62 is used to turn the audio on and off and a dial 61 is used to select the band of brain wave frequencies separated by appropriate filters. Position 61a of the dial 61 is the entire spectrum (T-Total) and positions 61b-61e are respectively the delta (1.5-3.5 Hz), theta (3.5-7.5 Hz), alpha (7.5-12.5 Hz) and beta (12.5-20 Hz) bands. Each of these, including the entire spectrum, generates a distinctive warble or series of tones in earphones 68. A person who has been trained can tell, by the intensity of the sequence of such tones, if the subject's brain waves sound normal or abnormal. Split half replication as in Version 1 may be used and significant abnormalities identified by a beep or other appropriate signal.

Version 3

As shown in FIG. 3, a rapid diagnosis may be obtained by using a hand-held QEEG device.

In Version 3 a headband 90 is applied to a subject. The headband 90 includes a self-attaching electrode set 50, preferably 3-16 electrodes, a pre-amplifier for each electrode, and an amplifier 52 for each pre-amplifier, an A/D converter 53, a micro-transmitter 54 (local battery operated radio transmitters). For example, in a war time battlefield situation the patches 90 may be applied to several (3-6) wounded soldiers within 50-100 feet of a blast site. An ear plug 91 is then inserted into the ear of each subject. The ear plug 91 may be a radio receiver activated by stimulator 72 or, alternatively, it self-generates a sound (click sound) at a selected frequency (F1), for example, at 40 clicks per second.

A patch 93 containing a self-attaching EKG electrode 94, A/D converter 95 and micro-transmitter 96 is placed on the subject's skin above the left collarbone. The amplified and digitized EKG heart waves are transmitted by the local radio transmitter 54 to the hand-held device 60.

Figure 4:
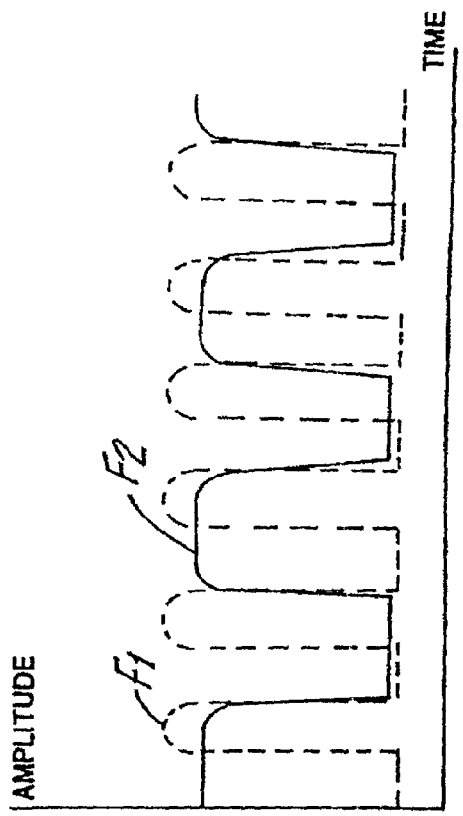
FIG. 4 is a chart showing the timing of two stimulations, namely, auditory clicks and somatosensory skin voltage pulses, which are simultaneous and out-of-phase.

The patient is preferably stimulated by audio clicks and vibratory or electrical voltage pulses to the skin to provide EPs by the stimulator 72 which is controlled by the microprocessor board 73. One of the electrodes is connected to the vertex as a reference ($C_z$ in 10/20 system). Preferably, to save time, the stimulations are given concurrently, at different frequencies and phase, as shown in FIG. 4. For example, a conductive bracelet or ring is adhered to the subject's skin and brief low voltage electrical pulses are transmitted to it. These provide a tingling sensation (somatosensory mode) at frequency F1. An earphone plug 91, which is a radio receiver, is inserted into the subject's ear and click sounds (auditory mode) are transmitted to the earphone at a different frequency F2, where F1 and F2 are different prime numbers.

The brain waves at the vertex, in a normal brain, will reflect both the F1 and F2 frequencies. The receiver unit 60, as in the first embodiment (Version 1) produces a Fast Fourier Transform (FFT) of the digital data, based on multiple 2.5 second segments. Separate FFTs are generated for the F1 and F2 frequencies, and their harmonics.

An "F ratio" is derived at each of the 4 frequency bands (alpha, beta, delta, theta). The F ratio is the ratio of power, Pstim, (mean squared) under stimulation, derived from a narrow band FFT, to a norm (the subject's power, Pref, at that frequency prior to stimulation, e.g., a self-norm). That F ratio may be tracked to determine if there are any changes in the subject's condition. Alternatively, the F ratio may be based on a comparison of the subject's brain waves to a normal group (population norm).

When time and the situation permit, split half replication may be optionally used to validate estimates of abnormality.

An F ratio may be determined in the different ways, as explained above in connection with Version 1. The F ratio is determined for both the F1 and F2 stimulation modes at each of the frequency bands. A trajectory is constructed using a sequence of measurements. If the subject is stable, those F ratios would stay the same and the first derivative of the trajectory would approach zero. The power generated at F1 and F2 includes their harmonics (preferably five harmonics).

Figure 9:

An LCD display 69 (FIG. 7 or 9) provides a visual indication of the patient's brain state in each frequency band, relative to normal values, by statistical assessment. The cortical response to auditory stimuli (at F1) and somatosensory stimuli (at F2) is similarly encoded in audio or visual output.

In addition, the receiver unit 60 has a row display 65 which shows amplitude, preferably a row of LCDS. If the brain wave amplitude (total or at each frequency band) is non-existent or low, the LCDs will indicate this appropriately. The frequency band to be displayed is selected by dial 61 or it cycles automatically, or all may be displayed as an array.

The FFT provides information in the frequency domain. The subject's brain waves are compared to a set of normal power spectra held in computer memory and generated using the same stimulus conditions. If the subject's power spectra differ significantly compared to the range of the predetermined norms, then an "abnormal" display is generated and displayed on alphanumeric display 69.

Version 4

Figure 5:
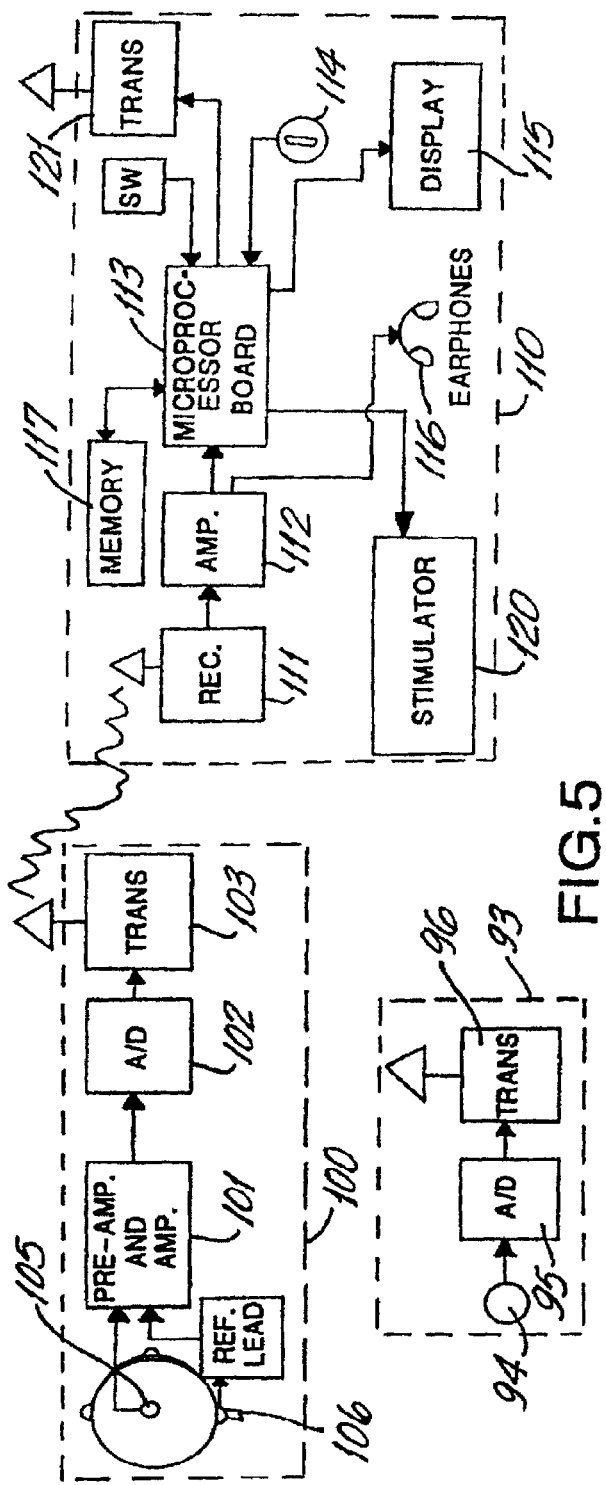
FIG. 5 is a block electronic schematic drawing of the system of the fourth embodiment.

In this embodiment, shown in FIG. 5, a single EEG electrode 105 is applied to the subject. The electrode is in an adhesive patch 100, about 2 cm in diameter, or in a headband. The patch 100 (or headband) also contains an amplifier 101 (pre-amplifier and amplifier), a battery, an A/D converter 102 and a micro-transmitter 103 (local radio transmitter). The transmitter 103 locally broadcasts the subject's brain waves as digital data, the data having modulated an FM or AM carrier at a selected frequency, or as modulations of the carrier by the analog EEG.

For example, the patches 100 may be applied to several (3-6) subjects within 50-100 of an emergency site. An ear plug 106 is inserted into the ear of each subject. The ear plug self-generates a sound (click sound) at a selected frequency (F1), for example, at 40 clicks per second, and may be a piezo-electric audio generator.

An adhesive patch 93, containing a self-attaching EKG electrode 94, A/D converter 95 and microtransmitter 96, is placed on the subject's skin above the left collarbone.

The hand-held receiver analyzer 110 includes a radio receiver 111, an amplifier 112, a microprocessor board 113, a dial 114, and a display 115, which function the same as the corresponding components in the embodiment of FIG. 3.

The microtransmitters 103 and 96 transmit short-range signals which provide the global condition of the subject's cerebral cortex and the brainstem (as evaluated by narrow band fast Fourier transform of the spontaneous EEG and the EEG activated by stimulation from the audio generator plug 106) and the waveshape of the EKG.

Using stored normative data from memory 117, based on age-matched normal controls and a baseline period (about 1 minute) of measurement of the initial state of the subject, the hand-held receiver 110 (Brain Stethoscope) will compute visual or auditory statistical evaluations of the global state of the subject's cortex and brainstem, based upon the narrow band FFT, and the R-R interval of the EKG. These quantitative evaluations (Z-scores relative to population norms) will be presented in visual LED display 115 or as audible signals on earphones 116, separately for each subject. The averaged Brainstem Auditory Evoked Response can be computed and the Peak I-IV measured to assess brainstem integrity. An updating trajectory display 115 will present the evolution of each measure, the slope (first derivative) of which will be automatically evaluated to assess whether the state is stable, improving or deteriorating. When time and circumstances permit, split-half replication may optionally be used to validate critical findings. Priorities, as to the care of the subjects, can then be assigned in an informed way.

On the trip to the hospital, in an ambulance, the history and updating trajectory, augmented by clinical assessments, would continue to be transmitted by transmitter 121 from the hand-held receiver 110. Samples of EEG Spectra/BAER/EKG waveshapes could be interrogated by the neurometric computer at the hospital (base station).

Assessment of spinal cord injury can be obtained by using the Brain Stem Somatosensory Evoked Potential (BSEP). Acquisition of BSEPs by the Brain Stethoscope can be accomplished by placing a rubber "cot" on the big toe of each foot and stimulating (via a stimulator 120), a pair of electrodes in the toe "cots" at a rate of about 17/sec (F2)—left toe; and 19/sec for (F3)—right toe. The spectral power at a midline forehead electrode, on the subject, at frequencies F2 and F3 will reflect the arrival of information at the cortex via the left and right medical lemniscal pathways. Cortical components and components of the BSEPs, at increasing latencies from 12 ms to 55 ms after each stimulus, will diminish and disappear depending upon the extent of spinal trauma. Finger tip electrodes (median nerve) can similarly be used to assess the level of injury from the 4th cervical vertebra (C4) and above. This will also estimate the extent of spinal cord injury and the compression caused by intrathecal hemorrhage.

The Brain Stethoscope constructs an "initial state norm" of all extracted EEG/Ep/EKG features during its initial set of measures, and this reference norm includes the variance of each measure. The state trajectory which it constructs utilizes the Z-transform (i.e., Z=[Present state minus initial state]/variance of initial state), or the F-ratio (present power/initial power). An automatic alarm can be set (auditory or visual) to alert attendants if any change in the state trajectory exceeds 2.56 standard deviation (P 0.01) toward further deterioration. This will provide monitoring of the subject during his transport to the hospital.

Version 5

Figure 6:
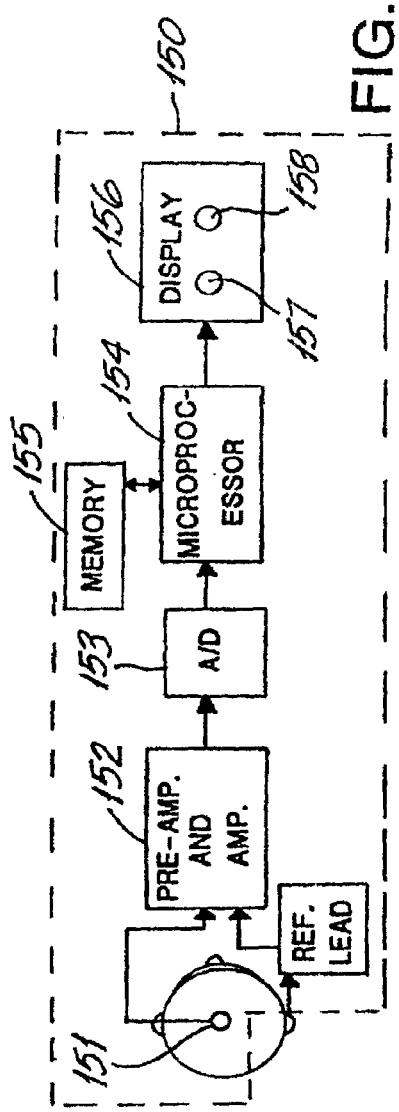
FIG. 6 is a block electronic schematic drawing of the entire instrument, including the computer analyzer and display, in a patch or headband.

In Version 5, shown in FIG. 6, the entire Brain Stethoscope is in a patch 150 or headband. Preferably, as in the prior embodiment of FIG. 5, an adhesive patch 150 has a single electrode 151 which preferably is placed midway between the ears, or less preferably on the forehead.

The patch 150 contains an electrode 151, an amplifier 152 (pre-amplifier and amplifier), battery, A/D converter 153, a microprocessor 154 having a computer memory 155, and a display 156. The entire patch is preferably less than 3 cm in diameter. The microprocessor 154 performs the QEEG analysis, described above, for the receiver of Version 4, and preferably produces a simple normal/abnormal result. Split-half replication may optionally be used to validate critical results, time permitting. That result is shown in the display 156 which is on the front face of the patch 150. The display 156 may be a green LED 157 ("normal") and red LED 158 ("abnormal").

In each of the above-described embodiments a reference lead (reference electrode) "REF/LEAD" should be used in addition to the active EEG electrode(s). Preferably the reference electrode is removably attached at the earlobe or mastoid (temporal bone behind ear). For example, a small 1-3 cm diameter adhesive patch containing a reference electrode may be adhered at the earlobe or mastoid. A wire runs from the reference electrode to the amplifier (pre-amplifier) which may be in a patch with the active electrode.

What is claimed is:

1. A medical system for analyzing brain waves of a subject, comprising:

a first active EEG (electroencephalograph) electrode detecting a subject's brain waves;

a stimulus generator providing to the subject sense stimuli in a plurality of stimulus modes to generate Evoked Potentials (EP), wherein the sense stimuli is delivered in multiple modalities at different prime number frequencies Fi to separate the Evoked Potentials;

a computer system receiving brain waves from the first electrode, said computer system comprising a memory unit to store reference data and a microprocessor configured to perform artifact rejection and data analysis of spontaneous EEG data and EP data, wherein the microprocessor is configured to determine, based on the data analysis, whether there is an injury to and dysfunction of at least one of the subject's spinal cord, brain stem and brain;

a visual output coupled to the microprocessor and configured to display the determination made by the microprocessor, the display being in the form of a normal versus abnormal indication; and a telemetric transmitter unit transmitting a result of the data analysis wirelessly to a remote receiving station for display and result storage.

2. The medical system of claim 1, further comprising an analog amplification channel connected to the active EEG.

3. The medical system of claim 2, further comprising a headgear on which the first electrode and the analog amplification channel are situated.

4. The medical system of claim 1, further comprising an analog-to-digital converter digitizing the amplified brain waves and supplying the digitized brain waves to the computer system.

5. The medical system of claim 1, wherein the data analysis is performed using Fast Fourier Transform (FFT) of narrow frequency bands, calculating power at each frequency band, and performing statistical evaluation by computing a Z-score, where $Z=(N-P)/6$, wherein N is a mean value of a normative distribution, P is a current measure from the subject and 6 is a standard deviation of a control age-matched population.

6. The medical system of claim 1, wherein FFT is used to compare a power at Fi when the stimulus generator is powered on to a power at Fi when the stimulus generator is powered off to compute an F-ratio for each frequency Fi, wherein the F-ratio=Pstim/Pref, where Pstim is the power under stimulation and Pref is the power prior to stimulation.

7. The medical system of claim 1, wherein the microprocessor is further configured to perform a split-half algorithm to improve signal-to-noise ratio.

8. The medical system of claim 1, further comprising a second active EEG electrode detecting a subject's brain waves, the computer system receiving brain waves from the second electrode.

9. The medical system of claim 1, wherein a first stimulus is adapted to be detected by a first sensory organ of the subject and a second stimulus is adapted to be detected by a second sensory organ of the subject.

10. The medical system of claim 9, wherein the first stimulus is one of a visual and an auditory stimulus.

11. The medical system of claim 9, wherein the second stimulus is one of a vibratory and an electrical pulse.

* * * * *